United States Patent [19]

Barrett et al.

[11] Patent Number: 5,269,290
[45] Date of Patent: Dec. 14, 1993

[54] PLANTAR FASCIOTOMY SURGICAL PROCEDURE

[76] Inventors: Stephen L. Barrett, 30503 Glenboro, Spring, Tex. 77386; Stephen V. Day, 1207 Spring Crest, Seabrook, Tex. 77586

[21] Appl. No.: 870,354

[22] Filed: Apr. 17, 1992

[51] Int. Cl.$^5$ ............................................. A61B 1/00
[52] U.S. Cl. ...................................... 128/4; 128/898
[58] Field of Search ......................... 128/4, 5, 6, 3, 20, 128/898; 606/170

[56] References Cited

U.S. PATENT DOCUMENTS

| | | |
|---|---|---|
| 4,461,281 | 7/1984 | Carson. |
| 4,607,621 | 8/1986 | Wheeler. |
| 4,815,464 | 3/1989 | Sanders. |
| 4,819,620 | 4/1989 | Okutsu ................................. 128/4 |
| 4,946,642 | 8/1990 | Watanabe. |
| 4,962,770 | 10/1990 | Agee et al. ........................... 128/898 |
| 5,029,573 | 7/1991 | Chow ..................................... 128/4 |

OTHER PUBLICATIONS

Forman and Green, The Role of Intrinsic Musculature in the Formation of Inferior Calcaneal Exostoses, *Clinics in Podiatric Medicine and Surgery*, Apr., 1990.
Turlik, Seronegative Arthritis as a Cause of Heel Pain, *Clinics in Podiatric Medicine and Surgery*, Apr., 1990.
Baerg, Calcaneal Decompression for Heel Pain, *Clinics in Podiatric Medicine and Surgery*, Jan., 1991.
Dailey, Differential Diagnosis and Treatment of Heel Pain, *Clinics in Podiatric Medicine and Surgery*, Jan., 1991.
Jacoby and Wolfe, Surgical Management of Recalcitrant Heel Pain, *Clinics in Podiatric Medicine and Surgery*, Jan., 1991.
Baxter and Thigpen, Heel Pain—Operative Results, *Foot & Ankle*, 1984.
Lutter, Surgical Decisions in Athletes' Subcalcaneal Pain, *The American Journal of Sports Medicine*, 1986.
O'Brien and Martin, A Retrospective Analysis of Heel Pain, *Journal of the American Podiatric Medical Association*, Aug., 1985.
Furey, Plantar Fasciitis, *The Journal of Bone and Joint Surgery*, Jul., 1975.
Hoffman and Thul, Fractures of the Calcaneus Secondary to Heel Spur Surgery, *Journal of the American Podiatric Medical Association*, May, 1985.
Shmokler, Bravo, Lynch and Newman, A New Use of Instrumentation in Fluoroscopy Controlled Heel Spur Surgery, *Journal of the American Podiatric Medical Association*, Apr., 1988.
Onuba and Ireland, Plantar Fasciitis, *Italian Journal of Orthopaedics and Traumatology*, Dec., 1986.
Kenzora, The Painful Heel Syndrome: All Entrapment Neuropathy, *Bulletin of the Hospital for Joint Diseases Orthopaedic Institute*, 1987.
LaMelle, Kisilewicz and Janis, Chronic Plantar Fascial Inflammation and Fibrosis, *Clinics in Podiatric Medicine and Surgery*, Apr., 1990.

(List continued on next page.)

Primary Examiner—Richard J. Apley
Assistant Examiner—Karen A. Jalbert
Attorney, Agent, or Firm—Barnes & Thornburg

[57] ABSTRACT

A new surgical technique, the Barrett-Day endoscopic plantar fasciotomy procedure, is used to relieve the symptoms of heel spur syndrome. The positioning of the plantar fascia ligament is determined, and the patient is prepared for surgery. A small, vertical incision is made in the medial side of the foot, and the adipose tissue is spread. A fascial elevator is inserted into the first incision to separate the plantar fascia from the surrounding tissue, creating a channel. A slotted canula and trocar is inserted into the channel, and a second incision is made on the lateral side of the foot, allowing the canula and trocar to substantially pierce the foot. The trocar is removed, and an endoscope is inserted into the canula through the medial portal. A cutting instrument is inserted into the lateral portal of the canula, and is used to release the plantar fascia from the heel bone. Once the plantar fascia has been released from the heel bone, the instruments are removed, and a bandage is placed around heel. The procedure allows the patient to immediately bear weight on the heel after the operation is complete.

34 Claims, 7 Drawing Sheets

OTHER PUBLICATIONS

Anderson and Foster, Operative Treatment of Subcalcaneal Pain, *Foot & Ankle*, Jun., 1989.

Ward and Clippiner, Proximal Medial Longitudinal Arch Incision for Plantar Fascia Release, *Foot & Ankle*, 1987.

Schepsis, Leach and Gorzyca, Plantar Fasciitis, *Clinical Orthopaedics and Related Research*, May, 1991.

Lester and Buchanan, Surgical Treatment of Plantar Fasciitis, *Clinical Orthopaedics and Related Research*, Jun., 1984.

Polisner, Early Ambulation After Minimal Incision Surgery for Calcaneal Spurs, *Clinics in Podiatry*, Jul., 1985.

Goulet, Role of Soft Orthosis in Treating Plantar Fasciitis, *Physical Therapy*, Apr., 1984.

Davidson and Copoloff, Neuromas of the Heel, *Clinics in Podiatric Medicine and Surgery*, Apr., 1990.

Beito, Krych and Harkless, Recalcitrant Heel Pain Traumatic Fibrosis versus Heel Neuroma, *Journal of the American Podiatric Medical Association*, Jul., 1989.

Meltzer, A Rational Approach to the Management of Heel Pain, *Journal of the American Podiatric Medical Association*, Feb., 1989.

Jay, Davis, Schoenhaus and Beckett, Calcaneal Decompression for Chronic Heel Pain, *Journal of the American Podiatric Medical Association*, Oct., 1985.

Contompasis, The Management of Heel Pain in the Athlete, *Clinics in Podiatric Medicine and Surgery*, Oct., 1986.

Amis, Jennings, Graham and Graham, Painful Heel Syndrome: Radiographic and Treatment Assessment, *Foot & Ankle*, 1988.

Correspondence—Treatable Causes of a Painful Heel.

Hill and Cutting, Heel Pain and Body Weight, *Foot & Ankle*, 1989.

Intenzo, Wapner, Park and Kim, Evaluation of Plantar Fasciitis by Three-phase Bone Scintigraphy, *Clinical Nuclear Medicine*, May, 1991.

Berkowitz, Kier and Rudicel, Plantar Fasciitis: MR Imaging, *Radiology*, 1991.

Sebes, The Significance of Calcaneal Spurs in Rheumatic Diseases, *Arthritis and Rheumatism*, Mar., 1989.

Lapidus and Guidotti, Painful Heel: Report of 323 Patients with 364 Painful Heels.

Bergmann, History and Mechanical Control of Heel Spur Pain, *Clinics in Podiatric Medicine and Surgery*, Apr., 1990.

Schwartz, Inferior Heel Spur Surgery, *Clinics in Podiatric Medicine and Surgery*, Apr. 1990.

Hepford, Minimal Incision Surgical Approach to Mechanical Heel Pain, *Clinics in Podiatric Medicine and Surgery*, Jan., 1991.

Snider, Clancy and McBeath, Plantar Fascia Release for Chronic Plantar Fasciitis in Runners, *The American Journal of Sports Medicine*, 1983.

Leach, Seavey and Salter, Results of Surgery in Athletes with Plantar Fasciitis, *Foot & Ankle*, 1986.

PLANTAR FASCIOTOMY SURGICAL PROCEDURE

BACKGROUND AND SUMMARY OF THE INVENTION

The present invention relates generally to a new podiatric surgical procedure. More particularly, the present invention relates to an endoscopic plantar fasciotomy surgical procedure.

Heel spur syndrome, or plantar fasciitis, is one of the most common foot pathologies for which a patient will seek treatment. Heel spur syndrome occurs approximately equally in both men and women, and can effect persons of all ages. It can effect persons who are regularly active as well as those who are relatively sedentary. This condition, often described by patients as a "stone bruise" in the heel of the foot, is usually worse in the morning, or when first standing after periods of rest. As the condition worsens, the heel can hurt even when not weight-bearing.

Heel spur syndrome is usually caused by a mechanical problem involving the structural alignment of the foot. There is a dense, fibrous band of tissue in the bottom of the foot known as the plantar fascia, which is connected to the heel bone and fans out toward the ball of the foot. The plantar fascia includes a medial band, a central band and a lateral band. Because of misalignment of the foot, excessive tension is placed on this band of tissue, causing inflammation and pain where the plantar fascia connects to the heel bone.

The inflammation of the plantar fascia can cause a spur or sediment to grow adjacent the heel bone. The patient can detect the spur, or "stone bruise" in the heel of the foot, and typically assumes that it is the cause of the pain. However, it has been known for many years that the pain is actually a result of the excessive tension placed on the plantar fascia, and not because of pressure placed on the spur.

While it is possible that heel spur syndrome will subside without treatment, in most cases the longer the patient waits to seek treatment the more chronic the condition becomes. Heel spur syndrome can be successfully treated without surgery in many cases. However, if pain and discomfort are still present after nonsurgical treatment, surgery is normally recommended.

There are generally two prior surgical techniques known which are used to relieve the tension on the plantar fascia and relieve the pain of heel spur syndrome. Perhaps the most common is a procedure where the spur is removed from the foot. A large incision, several centimeters in length, is made on the inside of the heel, which allows the surgeon access to the spur and the connection of the plantar fascia to the heel bone. In removing the spur from the heel, the plantar fascia is cut and released from its connection to the heel bone. This releases the tension in the plantar fascia, thus relieving the patient's pain.

This technique has several drawbacks. First, it has long been known that the resultant pain from heel spur syndrome is not caused by the spur, but by the tension in the plantar fascia. Thus, removing the spur is an unnecessary procedure. Furthermore, the spur is a deposit formed on the heel bone itself, and surgery on the bone can be more traumatic to the patient than surgery on tissue. Additionally, because of the large incision made in the heel and the cutting of the spur from the bone, patients are usually unable to bear any weight on the heel for 2-4 weeks after the surgery. This precludes an early return to work or recreational activity.

A second known technique for relieving the symptoms of heel spur syndrome is an operation whereby the plantar fascia is released from the heel bone, thus relieving the tension on the plantar fascia. However, in this technique, a large incision is made in the heel, allowing the surgeon to view the plantar fascia and its connection to the heel bone. Making such a large incision into the heel precludes the patient from bearing any weight on the foot for 2-4 weeks.

Further, techniques which limit the patient's ability to bear weight on the heel may also minimize the effectiveness of the operation. Once the plantar fascia is released from the heel bone, the tension in the fascia releases, easing the patient's pain. Bearing weight on the foot after the operation causes the plantar fascia to fan out, into an expanded configuration. This increases the gap between the plantar fascia and the heel bone. Scar tissue will then grow to reconnect the plantar fascia to the heel bone across the gap. If the patient is able to bear weight on the foot immediately after the operation, the scar tissue will grow from the expanded state, thus creating a longer plantar fascia, which is less subject to tension. If the patient must experience several weeks of post-operative immobility, the plantar fascia remains in a contracted state. Thus, when the scar tissue grows to reconnect the plantar fascia to the heel bone, the plantar fascia may be subject to the same tension as previously experienced.

Accordingly, it is an object of the present invention is to provide a heel spur syndrome surgical procedure which minimizes the length of time necessary for patient recovery and resumption of normal activities.

Another object of the present invention is to provide a heel spur syndrome surgical procedure which reduces the tension experienced by the plantar fascia.

A further object of the present invention is to provide a heel spur syndrome surgical procedure which minimizes the cost of treating the condition.

Yet another object of the present invention is to provide a heel spur syndrome surgical procedure which minimizes the surgical trauma incident to treatment of heel spur syndrome.

A still further object of the present invention is to provide a heel spur syndrome surgical procedure which can be readily performed using commercially available equipment and conventional medical techniques.

These and other objects of the present invention are attained by the provision of an endoscopic plantar fasciotomy surgical procedure which utilizes a small incision, normally approximately 4 millimeters in length, in the heel of the patient's foot. Generally, this procedure can be performed in an office comfortably under a local anesthetic. A first incision, preferably cut in a vertical direction, approximately 4 millimeter in length, is made in the medial side of the foot. Adipose tissue is removed, and a fascial elevator is inserted into the first incision to create a channel laterally in the foot. Next, a canula and trocar are inserted into the first incision. A second incision is made on the lateral side of the foot so that the trocar and canula can substantially pierce the foot. The trocar is then removed and an endoscope is placed into the canula through the medial portal. A cutting instrument is placed into the canula from the lateral portal, and the plantar fascia is cut thereby adjacent its connection to the heel bone. To assure that a proper release of the plantar fascia has been achieved, a hook probe is inserted into the canula and moved laterally across the plantar fascia along the area where the fascia has been severed. The instruments are then removed from the canula, and the canula is removed from the foot. A bandage is placed on the foot, and the patient is usually immediately able to bear weight on the foot. In most cases, minimal, if any, pain medication is required.

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
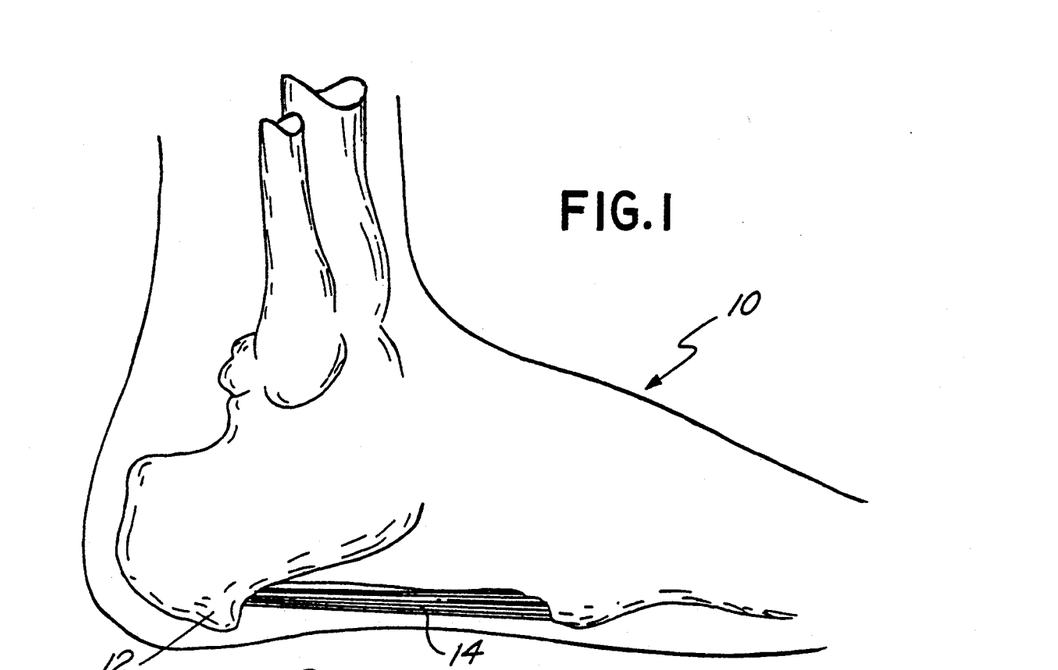
FIG. 1 is a side view of the heel portion of a foot showing the plantar fascia connected to the heel bone.

Referring now to the drawings, in which like-referenced characters indicate corresponding elements throughout the several views, attention is first directed to FIG. 1 which illustrates a side view of the heel portion of a foot, generally identified by the reference numeral 10. Foot 10 includes a number of connected bones including heel bone 12 which is located rearward and downward in foot 10. Heel bone 12 is connected to plantar fascia 14, which is a dense band of tissue extending forwardly and spreading out toward the toes.

Figure 2:
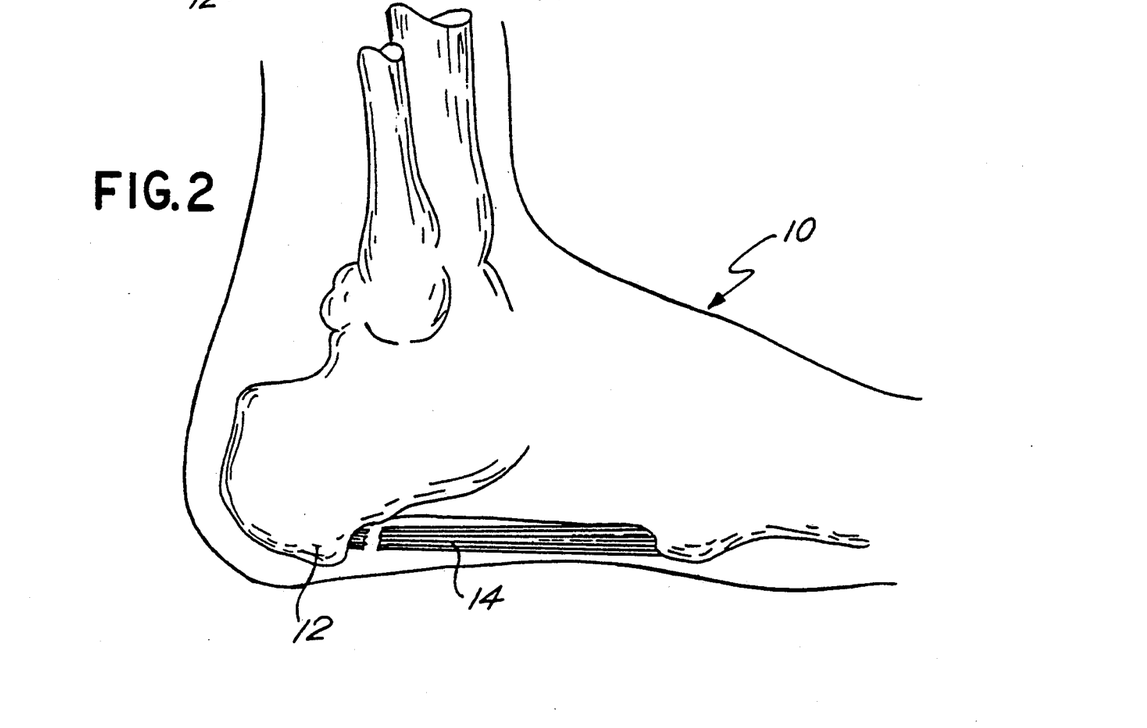
FIG. 2 is a side view of the heel portion of a foot showing the plantar fascia released from the heel bone.
Figure 3:
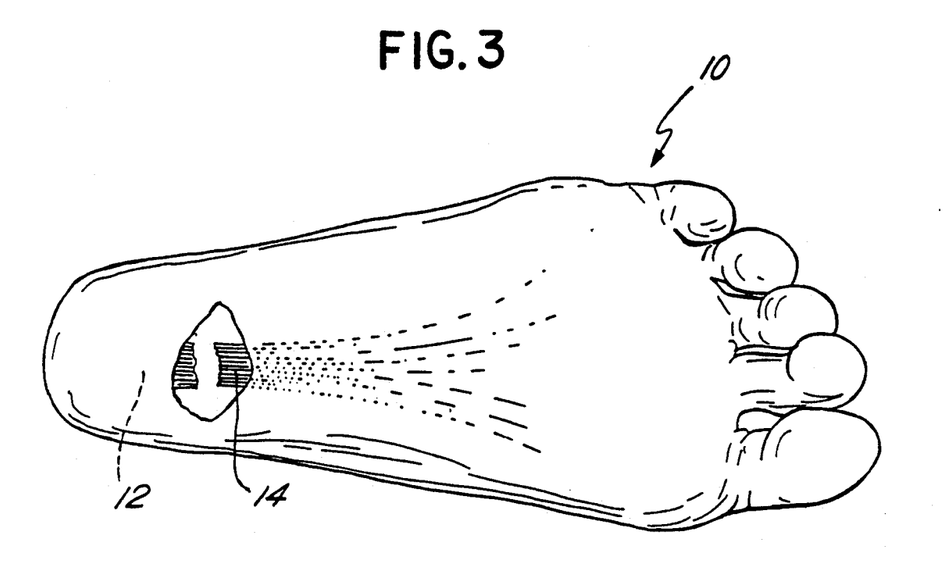
FIG. 3 is a bottom view of a foot showing the plantar fascia released from the heel bone.

Utilizing the preferred endoscopic plantar fasciotomy procedure, the operation may be conducted in-office, on an out-patient basis. The patient is weight-bearing immediately after the procedure is performed, thus allowing for expansion of plantar 14 fascia and proper growth of scar tissue between plantar fascia 14 and heel bone 12. This technique also allows the patient to return home immediately after the operation, and return to normal activities within several days.

Figure 7:
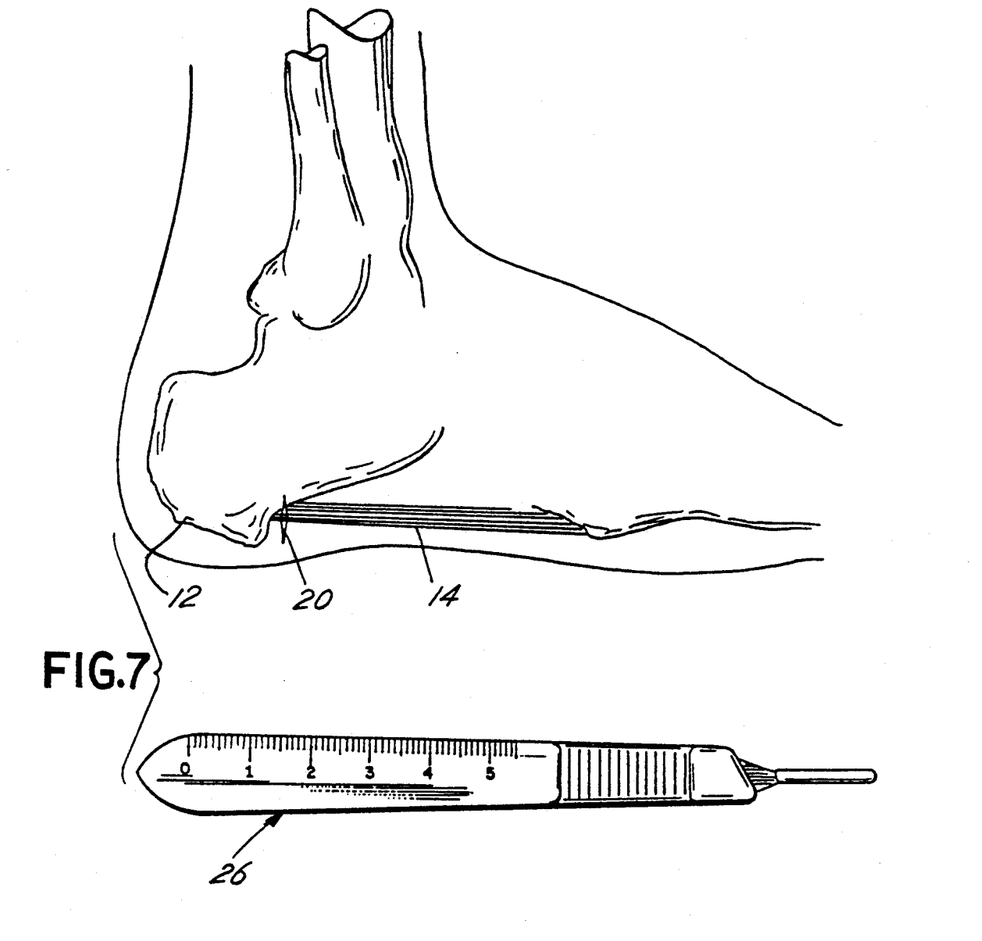
FIG. 7 is a side view of a foot showing the approximate location of the first incision and a metric ruler.

While other similar instrumentation may be used to effectively perform this surgical technique, the applicants have found particular instrumentation to be preferable. For example, to determine the placement of the medial incision in the foot, metric steel ruler 26 is used rather than the calibrations on a standard blade handle.

Preferably, a thin surgical marker is used to mark the position of the medial incision, and a standard #15 blade and handle is used to make the medial incision and the lateral incision. Other small instrumentation used to perform the surgical procedure include a small pair of blunt tipped dissecting scissors with a slight curve, a fascial elevator, a slotted canula and trocar, a pair of Adson forceps and a small needle holder.

To perform this procedure, the applicants prefer using a 30 degree angled 2.7 millimeter×67 millimeter focusing video arthroscope with a 35 millimeter focal length. This scope is coupled to a two-camera system with compatible light source, thus providing an image on a high resolution medical grade television monitor such as the 25-inch resolution medical grade television monitor manufactured by Sony Corporation. In addition, a quality VHS format video recorder can provide hard copy, real time documentation of the procedure.

Local anesthesia is preferred, due to the minimal invasiveness of the surgical technique. The use of local anesthesia is also beneficial in that it allows the patient to bear weight on the foot immediately after the operation. This benefit is not always available with other forms of anesthesia. Furthermore, because the endoscopic plantar fasciotomy surgical procedure is a minimally traumatic procedure, the exposure to higher risks associated with other anesthetics is not needed. Furthermore, local anesthesia can be much more cost effective than other forms of anesthesia.

Figure 4:
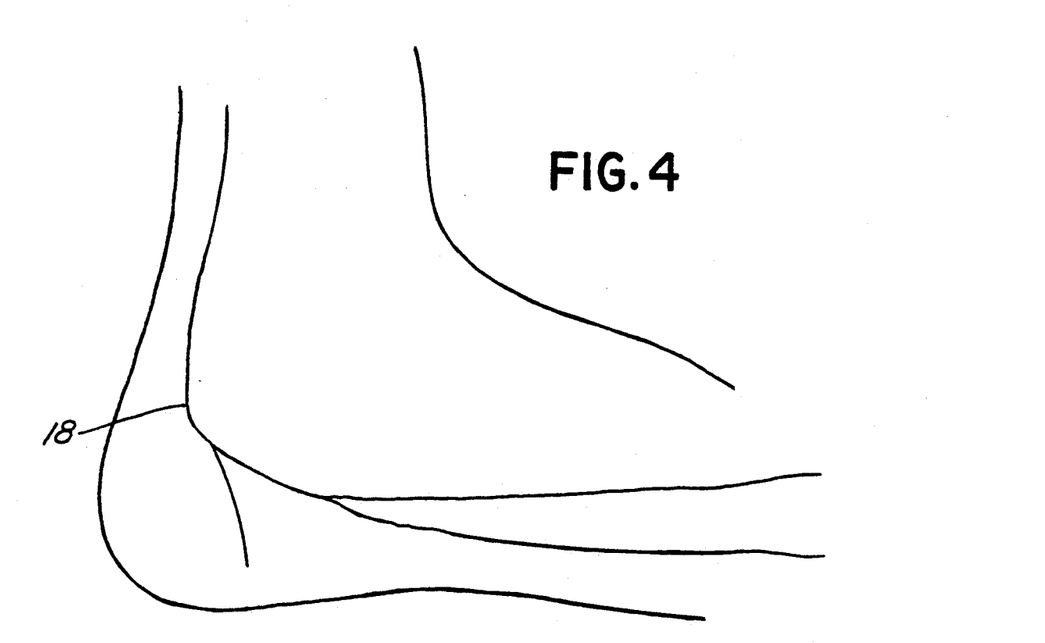
FIG. 4 is a side view of a foot showing the positioning of the tibial nerve.
Figure 5:
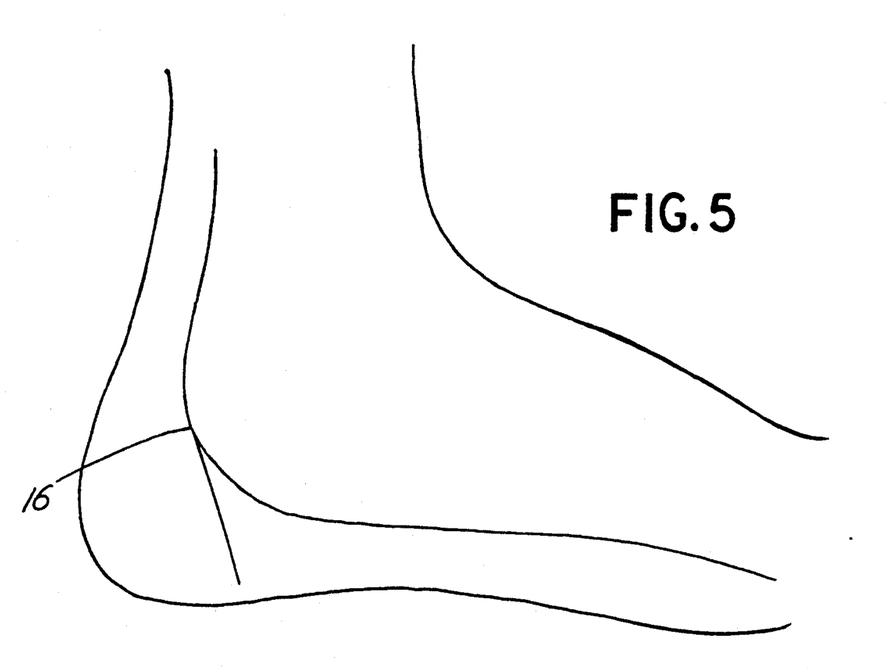
FIG. 5 is a side view of a foot showing the positioning of the sural nerve.

A preferred method of anesthetizing the foot includes infiltrating approximately 3-6 cubic centimeters with a 1:1 ratio of 0.5% bupivicaine plain with 2% lidocaine plain into the area of posterior tibial nerve 16 and sural nerve 18. The applicants have found that it is preferable to allow 30-45 minutes to achieve local blockage of the heel, before the patient is moved into the operating room.

Occasionally, some superficial branches coming medially off the superficial peroneal nerve or the saphenous nerve may also need to be blocked. Before attempting to block the latter, the applicants have found it beneficial to initially perform the sural and posterior tibial nerve block and allow several minutes before ascertaining anesthesia. By blocking these two nerves completely, adequate anesthesia is normally attained for the patient. If, however, there are still areas that are not to an acceptable level of anesthesia, the applicants would not recommend infiltration of local anesthetic into the area where the surgical procedure is to be performed unless absolutely necessary. Such local infiltration of anesthesia has been found to cause serious visual impairment during the endoscopy procedure. Instead, the sural and posterior tibial nerves should be further anesthetized.

After anesthetizing the patient, the endoscopic plantar fasciotomy surgical procedure of the present invention continues with the pre-operative planning of the operation. First, the location of plantar fascia 14 is determined. It is preferable to determine the actual position of plantar fascia 14 using a non weight-bearing lateral projection radiograph taken a short period of time before surgery. The radio-opaque line of plantar fascia 14 should be apparent in such a radiograph. The shadow, or grey line, that corresponds to the plantar fascia should be followed from anterior to posterior as it inserts into the medial calcaneal tubercle. It is at this point that a reference position is delineated approximately two to three millimeters below the insertion of the fascia into the tubercle. If a large inferior calcaneal exostosis is present, this reference position should be placed on the same vertical level, but just anterior to the distal aspect of the calcaneal exostosis.

Once this reference position has been established, a measurement is made from the posterior skin surface of the heel to the reference position anteriorly, and another measurement is made from the reference position vertically and inferiorly to the plantar skin surface. With these measurements, the corresponding placement of the reference position can be mapped out on the patient in the operating room.

The placement of first incision 20 should allow for the trocar to be placed inferiorly to plantar fascia 14. If the reference position is placed too high, an adequate fascial release may not be achieved laterally. Conversely, if the placement of the incision is too low, adequate release of the plantar fascia may not be achieved.

Figure 6:
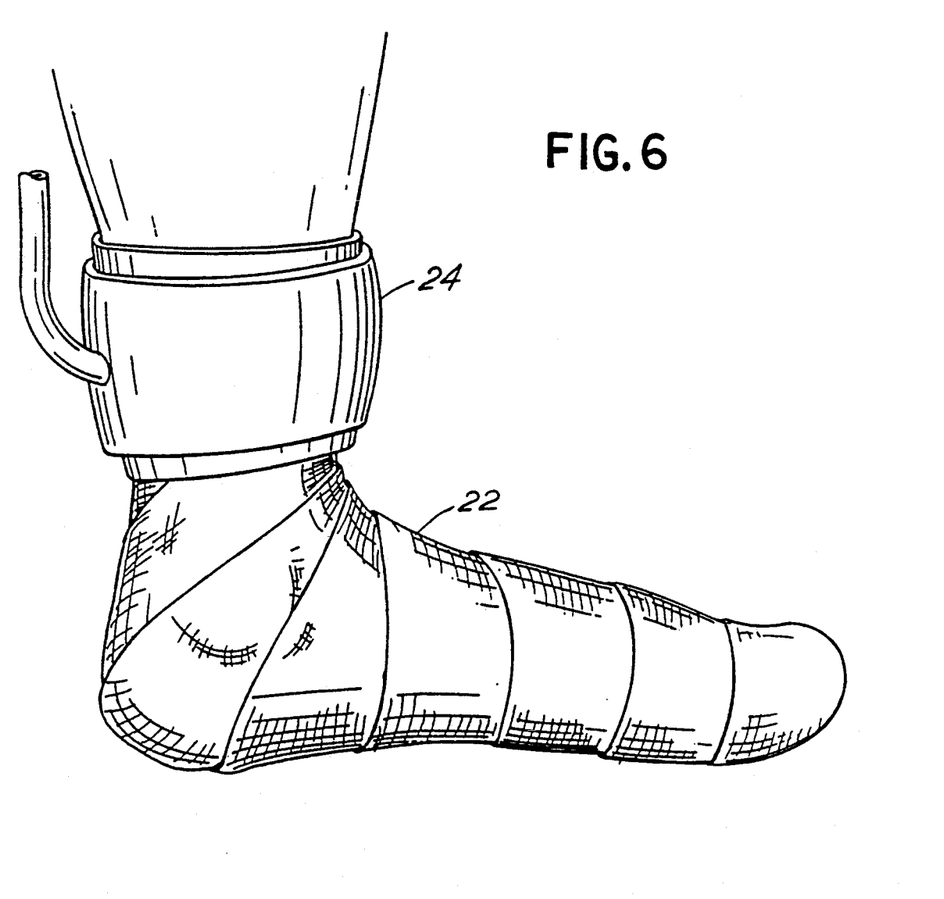
FIG. 6 is a side view of a foot having a tourniquet and a bandage thereon.

Once these measurements are completed, the patient is placed onto the operating room table in a supine position, and prepared and draped in the usual aseptic manner. The anesthesia is ascertained by use of Adson forceps with teeth to provide a noxious stimulus in the area of the surgery. The anesthesia should be checked medially, laterally and plantarly. Exsanguination of the foot is then achieved, preferably with Esmark bandage 22, followed by inflation of ankle tourniquet 24 to a pressure of approximately 250 millimeters of mercury.

Once the anesthetic blockage is confirmed, and exsanguination is achieved, first incision 20 is made into the skin. While any blade or cutting mechanism may be used, the applicants have found that a #15 blade is preferred. The placement of first incision 20 corresponds to the reference mapped out on the patient. It is preferred that first incision 20 be approximately 4 millimeters in length. It is further preferred that the incision be made substantially vertically; that is, substantially transverse to the longitudinal direction of the foot and plantar fascia 14. It is also preferred that first incision 20 be made in the medial side of the foot. Next, the adipose tissue is spread. This can be accomplished by introducing blunt dissecting scissors into first incision 20, and spreading the tissue. Once this is accomplished, the medial aspect of plantar fascia 14 can be palpated with the tips of the scissors. The dissecting scissors can then be introduced deeper, along the inferior surface of plantar fascia 14. At this point of the procedure the inferior plantar convexity of plantar fascia 14 can be appreciated. This use of the dissecting scissors creates a channel into which canula 34 will be introduced.

Figures 8, 9:
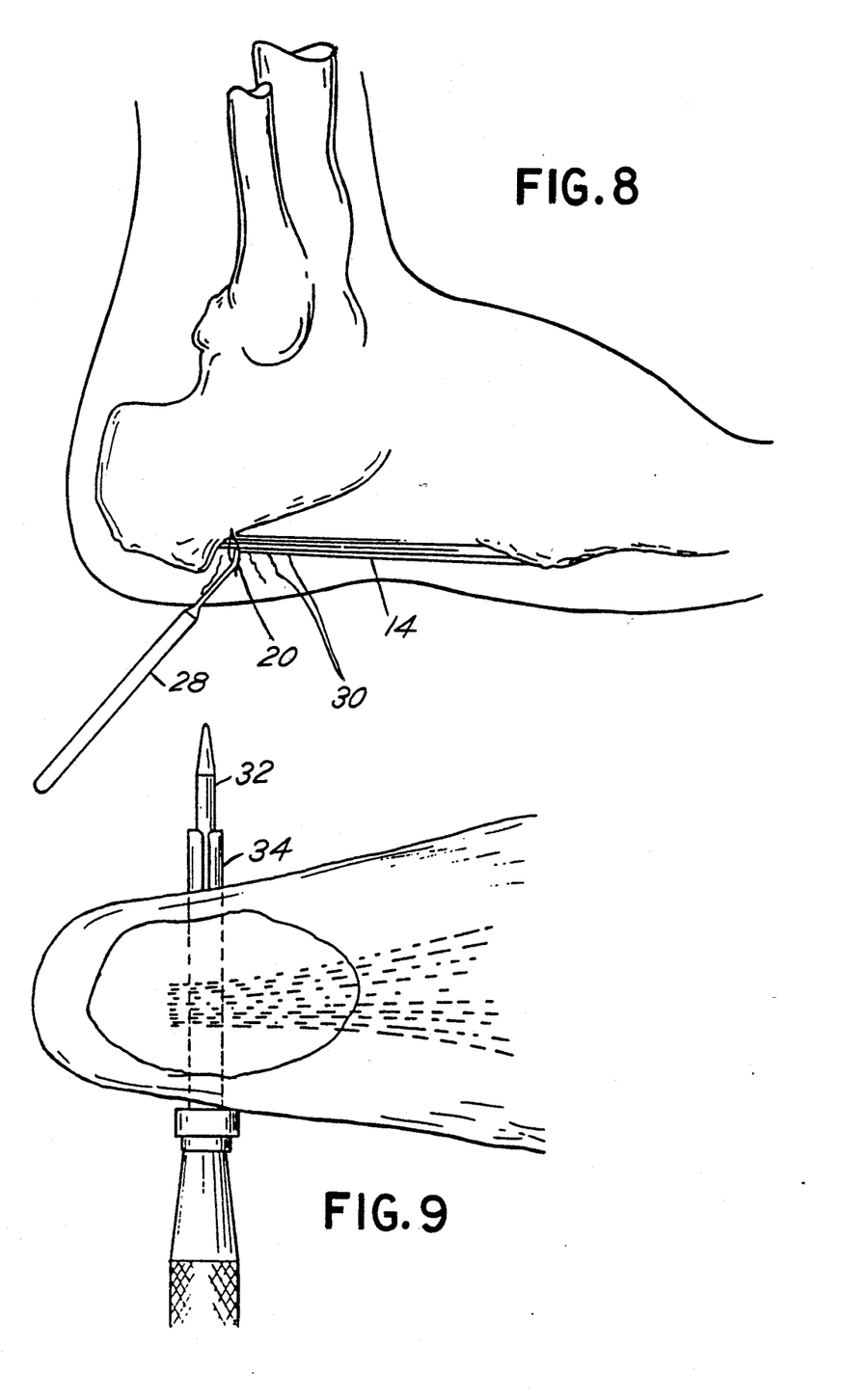
FIG. 8 is a side view of a foot showing a fascial elevator inserted into the first incision and the location of the spiral septa.
FIG. 9 shows a bottom view of a foot showing the trocar and canula substantially piercing the foot.

After using the dissecting scissors the channel can be completed by use of fascial elevator 28. At this point, the full convexity of plantar fascia 14 can be appreciated. It is sometimes necessary to release some of the fibrous spiral septa 30 extending into the heel fat pad inferiorly at the lateral aspect of the fascia. To do this, the end of fascial elevator 28 is palpated laterally through the skin before trocar 32 is placed into the heel. If this is not accomplished, then during the placement of trocar 32 an incomplete channel may cause inferior placement of canula 34 at the lateral aspect of plantar fascia 14 and a complete lateral release will be more difficult to accomplish.

Trocar 32 and canula 34 are then placed into the channel along the inferior surface of plantar fascia 14 extending toward the lateral aspect of the heel. Care should be taken to avoid splitting the fascia at either the junction of the medial and central bands or at the junction of the central and lateral bands with trocar 32. If this occurs an incomplete release may occur if the improper placement is not recognized by the surgeon. In addition, incorrect placement may also cause additional, unnecessary tissue trauma.

Once the tip of trocar 32 can be palpated through the skin, a second incision is made on the lateral side of the foot, approximately opposite the first incision, allowing trocar 32 and canula 34 to be placed completely through the heel. Preferably, this second incision is also made with a #15 blade, and is made vertically, approximately 4 millimeters in length. Trocar 32 is then withdrawn from canula 34. Several sterile cotton tipped applicators can then be run through canula 34 to remove any adipose tissue that remains in the tube.

Figure 10:
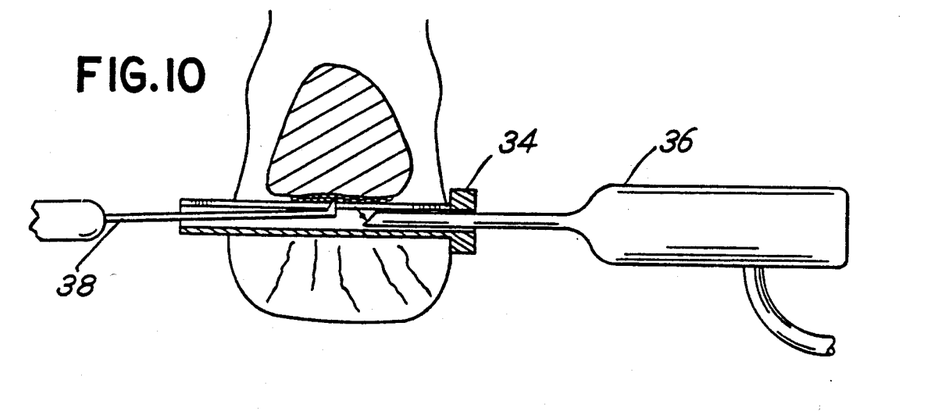
FIG. 10 is a rear view of a foot showing an endoscope and cutting instrument inserted into the canula.

Endoscope 36 is then placed into canula 34, preferably from the medial portal. At this time, the entire width of plantar fascia 14 can be viewed from medial to lateral. If there is any visual impairment due to unwanted adipose tissue, this can be removed with suction biting forceps. Two anatomical locations should then be identified, the medial plantar fascial investment and the lateral plantar fascial investment.

With endoscope 36 focused at the medial plantar fascial investment, retrograde knife 38 is introduced into the lateral portal of canula 34 extending across the fascia medially until it is brought into view. By placing dorsal pressure on retrograde knife 38, the medial investment is then "hooked." Gentle retrograde pressure is used to bring retrograde knife 38 laterally, and begin the severance, or incision, of plantar fascia 14 from heel bone 12. An assistant surgeon should monitor the fascial separation with the endoscope by moving endoscope 36 from medial to lateral.

Figure 11:
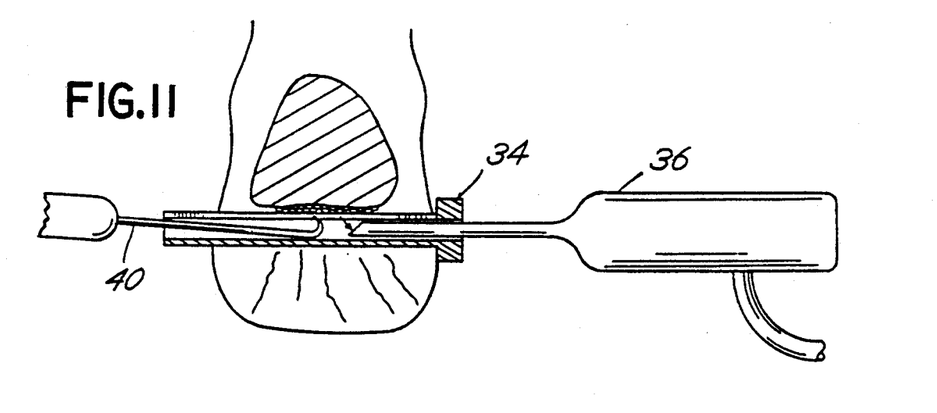
FIG. 11 is a rear view of a foot showing an endoscope and a hook probe inserted into the canula.

The surgeons should closely observe the monitor in order to ensure a complete fascial release. In most cases, a complete fascial release will not be achieved with one pass of retrograde knife 38. If complete release is not achieved in a single pass, several passes may be made. A complete release will allow the muscle belly below plantar fascia 14 to be viewed on the monitor. Thus, the red or violaceous muscle belly will be positioned between the two brilliant white ends of the released fascia. The intermuscular septa should be viewed and identified during the procedure. Then, from medial to lateral, across the inferior surface of plantar fascia 14, the two severed ends of the fascia should be observed to ensure a complete fascial release. If this is difficult to distinguish, probe 40 can be used to tease the tissue so the muscle belly can be observed. If an area of incomplete release is identified, a knife can be used to release any remaining fibers of plantar fascia 14 through use of gentle dorsal pressure.

Once the surgeon has accomplished a "complete" release, endoscope 3 is placed into the lateral portal of canula 34 and the blade 38 is inserted into the medial portal of canula 34 and the severing process is repeated. This helps the surgeon verify that a complete release has in fact been performed and also provides the surgeon with a different visual perspective. This different perspective is particularly helpful in regard to viewing the medial plantar fascial investment. The medial band is the thickest band of the three bands of the plantar fascia, and medially it curves superiorly to invest the abductor hallucis muscle. From the lateral perspective this can be appreciated and any remaining fibers can be appropriately released.

Figure 12:
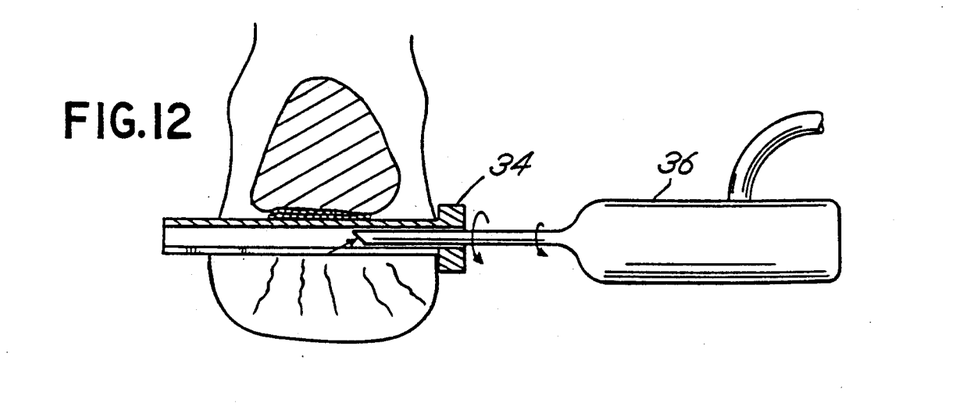
FIG. 12 is a rear view of a foot showing rotation of the canula and endoscope.

Once the surgeon is assured that a complete release has been performed, canula 34 should be rotated approximately 180° to allow the surgeon to view plantarly if plantar fascia 14 has been penetrated and split. This is shown in FIG. 12. Canula 34 should then be rotated another approximately 180° to its original placement and probe 40 can be inserted into canula 34 to separate the cut ends of plantar fascia 14.

At this time the procedure is complete and the instrumentation is then removed from canula 34. A sterile lavage through canula 34 is performed, and the canula removed. Preferably two to three interrupted 5-0 prolene sutures are then used to close the skin incisions. Three cubic centimeters of 0.5% bupivicaine plain, and one cubic centimeter of dexamethasone phosphate is infiltrated into the area. A small compression gauze bandage is then placed over the incisions, and ankle tourniquet 24 is deflated.

Although the present invention has been described above in detail, the same is by way of illustration and example only and is not to be taken as a limitation on the present invention. The scope and content of the present invention are defined only by the terms of the appended claims.

What is claimed is:

1. A surgical method of performing a plantar fasciotomy whereby a plantar fascia is incised from its connection to the heel bone, comprising the steps of:
   making a first incision on one side of a foot anteriorly adjacent a distal portion of the heel bone and inferiorly of the plantar fascia;
   inserting a fascial elevator into said first incision to separate said plantar fascia from surrounding tissue;
   projecting said fascial elevator laterally through said foot to create a channel therein, said channel extending along an inferior surface of the plantar fascia;
   removing said fascial elevator from said first incision;
   inserting a canula having a trocar therein through said first incision into said channel;
   making a second incision in said foot;
   projecting said canula and trocar through said second incision, whereby said canula and trocar substantially pierce said foot;
   removing said trocar from said canula;
   inserting an endoscope into said canula to allow projected viewing of the anatomy of said plantar fascia;
   inserting a cutting instrument into said canula; and
   manipulating said cutting instrument to incise said plantar fascia from said heel bone.

2. The method according to claim 1 including the step of taking a pre-operative radiograph of said foot to identify the location of said plantar fascia prior to making said first incision.

3. The method according to claim 2 including the step of anesthetizing said foot with a local anesthetic prior to making said first incision.

4. The method according to claim 3 including the step of mapping incision coordinates on said foot prior to making said first incision.

5. The method according to claim 4 including the step of exsanguinating said foot by tightly wrapping said foot with a bandage and placing a tourniquet around the ankle prior to making said first incision.

6. The method according to claim 5 wherein said bandage is an Esmark bandage.

7. The method according to claim 6 wherein said tourniquet is inflatable.

8. The method according to claim 7 including the step of inflating said tourniquet to approximately 250 millimeters of mercury of pressure prior to making said first incision.

9. The method according to claim 1 wherein said first incision and said second incision are cut substantially transverse to said plantar fascia.

10. The method according to claim 9 wherein said first incision and said second incision are each approximately 4 millimeters in length.

11. The method according to claim 10 wherein said first incision is cut in the medial side of said foot.

12. The method according to claim 11 wherein said second incision is cut in the lateral side of said foot.

13. The method according to claim 1 including the step of introducing dissecting scissors into said canula through said first incision to spread any surrounding adipose tissue prior to inserting said fascial elevator into said first incision.

14. The method according to claim 13 including the step of palpating the medial aspect of said plantar fascia with the tips of said dissecting scissors after said dissecting scissors are inserted into said first incision.

15. The method according to claim 14 including the step of inserting said dissecting scissors adjacent the inferior surface of said plantar fascia after palpating the medial aspect of said plantar facia.

16. The method according to claim 15 including the step of removing said dissecting scissors from said canula prior to inserting said fascial elevator into said first incision.

17. The method according to claim 16 further including the step of releasing at least a portion of the fibrous spiral septa extending into the heel pad inferiorly, at the lateral aspect of said plantar fascia prior to inserting said fascial elevator into said first incision.

18. The method according to claim 1 including the step of running an applicator through said canula to remove any adipose tissue remaining in said canula after removing said trocar from said canula.

19. The method according to claim 1 wherein said endoscope is inserted into said canula from the medial side of said foot.

20. The method according to claim 19 wherein said cutting instrument is inserted into said canula through the lateral side of said foot.

21. The method according to claim 20 further including the step of removing any undesired adipose tissue after inserting said cutting instrument into said canula.

22. The method according to claim 21 whereby manipulating said cutting instrument to incise said plantar fascia includes applying dorsal pressure to said cutting mechanism to move said cutting instrument laterally against said plantar fascia to sever said plantar fascia from said heel bone.

23. The method according to claim 22 whereby said cutting instrument is moved laterally against said plantar fascia a series of times to ensure a complete release of said plantar fascia from said heel bone.

24. The method according to claim 23 including the step of removing said cutting instrument from said canula after it is used to sever said plantar fascia from said heel bone.

25. The method according to claim 24 including the step of inserting a hook probe into said canula through the lateral side of said foot and moving said hook probe laterally through the cut made by said cutting instrument to confirm that a complete release of said plantar fascia from said heel bone has occurred after removing said cutting instrument from said canula.

26. The method according to claim 25 including the step of removing said hook probe and said endoscope from said canula.

27. The method according to claim 26 including the step of inserting said enscope into said canula through the lateral side of said foot and inserting said cutting instrument into said canula through the medial side of said foot.

28. The method according to claim 27 including the step of applying dorsal pressure to said cutting instrument to move said cutting instrument laterally against said plantar fascia to sever said plantar fascia from said heel bone.

29. The method according to claim 28 whereby said cutting instrument is moved laterally against said plantar fascia several times to ensure that said plantar fascia is severed from said heel bone.

30. The method according to claim 29 including the step of removing said cutting instrument from said canula.

31. The method according to claim 30 including the step of inserting a hook probe into said canula through the medial side of said foot to confirm that a complete release of said plantar fascia from said heel bone has been performed.

32. The method according to claim 1 including the step of rotating said canula approximately 180° within said channel to view plantarly whether said fascia has been penetrated and severed from said heel bone after incising said plantar fascia from said heel bone.

33. The method according to claim 32 including the step of rotating said canula another approximately 180° to allow for medial and lateral viewing and to allow for separation of the severed end of said plantar fascia.

34. The method according to claim 1 wherein said cutting instrument is a #15 blade.

* * * * *

REEXAMINATION CERTIFICATE (2914th)
United States Patent [19]
Barrett et al.

[11] B1 5,269,290
[45] Certificate Issued Jun. 11, 1996

[54] PLANTAR FASCIOTOMY SURGICAL PROCEDURE

[75] Inventors: Stephen L. Barrett, Spring; Stephen V. Day, Seabrook, both of Tex.

[73] Assignee: Instratek Incorporated, Houston, Tex.

Reexamination Request:
No. 90/003,623, Nov. 7, 1994

Reexamination Certificate for:
Patent No.: 5,269,290
Issued: Dec. 14, 1993
Appl. No.: 870,354
Filed: Apr. 17, 1992

[51] Int. Cl.$^6$ ................................................ A61B 1/00
[52] U.S. Cl. ........................................ 600/183; 128/898
[58] Field of Search .................... 128/4, 6, 898, 128/20, 3, 5; 606/170; 600/183, 101

[56] References Cited

U.S. PATENT DOCUMENTS 5,029,573  7/1991  Chow .................................... 128/4

OTHER PUBLICATIONS

Barrett, Day and Brown, Endoscopic Plantar Fasciotomy: Preliminary Study with Cadaveric Specimens, *The Journal of Foot Surgery*, 1991, pp. 170–172.
Barrett and Day, Endoscopic Plantar Fasciotomy for Chronic Plantar–Fasciitis/Heel Spur Syndrome: Surgical Technique—Early Clinical Results, *The Journal of Foot Surgery*, 1991, pp. 568–570.
Barrett, The Barrett–Day Endoscopic Plantar Fasciotomy workshop manual with forward by Brown.
Polisner, Early Ambulation After Minimal Incision Surgery for Calcaneal Spurs, *Clinics in Podiatry*, 1985, pp. 497–502.
Resnick and Miller, Endoscopic Carpal Tunnel Release Using the Subligamentous Two–portal Technique, *Contemporary Orthopaedics*, 1991, pp. 269–277.
Hepford, Minimal Incision Surgical Approach to Mechanical Heel Pain, *Clinics in Podiatric Medicine and Surgery*, 1991 pp. 167–185.
Chow, Endoscopic Release of the Carpal Ligament: A New Technique for Carpal Tunnel Syndrome, *Arthroscopy, The Journal of Arthroscopic & Related Surgery*, 1989, pp. 19–24.

*Primary Examiner*—R. J. Apley

[57] ABSTRACT

A new surgical technique, the Barrett-Day endoscopic plantar fasciotomy procedure, is used to relieve the symptoms of heel spur syndrome. The positioning of the plantar fascia ligament is determined, and the patient is prepared for surgery. A small, vertical incision is made in the medial side of the foot, and the adipose tissue is spread. A fascial elevator is inserted into the first incision to separate the plantar fascia from the surrounding tissue, creating a channel. A slotted canula and trocar is inserted into the channel, and a second incision is made on the lateral side of the foot, allowing the canula and trocar to substantially pierce the foot. The trocar is removed, and an endoscope is inserted into the canula through the medial portal. A cutting instrument is inserted into the lateral portal of the canula, and is used to release the plantar fascia from the heel bone. Once the plantar fascia has been released from the heel bone, the instruments are removed, and a bandage is placed around heel. The procedure allows the patient to immediately bear weight on the heel after the operation is complete.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–12 and 18–34 is confirmed.

Claims 13, 16 and 17 are determined to be patentable as amended.

Claims 14 and 15, dependent on an amended claim, are determined to be patentable.

13. The method according to claim 1 including the step of introducing dissecting scissors into [said canula through] said first incision to spread any surrounding adipose tissue prior to inserting said fascial elevator into said first incision.

16. The method according to claim 15 including the step of removing said dissecting scissors from said [canula] *first incision* prior to inserting said fascial elevator into said first incision.

17. The method according to claim 16 further including the step of releasing at least a portion of the fibrous spiral septa extending into the heel pad inferiorly, at the lateral aspect of said plantar fascia prior to inserting said [fascial elevator] *canula and trocar* into said first incision.

* * * * *